United States Patent [19]
Colvin

[11] Patent Number: 6,112,004
[45] Date of Patent: Aug. 29, 2000

[54] EMISSION MICROSCOPY SYSTEM AND METHOD

[76] Inventor: James Barry Colvin, 36217 Worthing Dr., Newark, Calif. 94560

[21] Appl. No.: 09/181,117

[22] Filed: Oct. 28, 1998

Related U.S. Application Data

[60] Provisional application No. 60/087,553, Jun. 1, 1998.

[51] Int. Cl.[7] .................................................. G02B 6/06
[52] U.S. Cl. ........................... 385/116; 385/117; 385/902
[58] Field of Search .......................... 385/31, 115, 116, 385/117, 147, 902

[56] References Cited

U.S. PATENT DOCUMENTS

| | | | |
|---|---|---|---|
| 4,660,925 | 4/1987 | McCaughan, Jr. | 350/96.15 |
| 4,811,090 | 3/1989 | Khurana | 358/93 |
| 4,997,259 | 3/1991 | Ichimura et al. | 385/115 |
| 5,044,717 | 9/1991 | Levatter | 385/33 |
| 5,140,289 | 8/1992 | Andrieu et al. | 333/256 |
| 5,263,110 | 11/1993 | Anderson | 385/117 |
| 5,303,373 | 4/1994 | Harootian, Jr. | 385/115 |
| 5,475,316 | 12/1995 | Hurley et al. | 324/750 |
| 5,522,006 | 5/1996 | Takeuchi et al. | 385/139 |
| 5,534,000 | 7/1996 | Bruce | 606/15 |
| 5,536,265 | 7/1996 | van den Bergh et al. | 606/2 |
| 5,548,670 | 8/1996 | Koike | 385/27 |
| 5,632,767 | 5/1997 | Sinofsky | 607/89 |
| 5,695,583 | 12/1997 | van den Bergh et al. | 156/153 |
| 5,698,474 | 12/1997 | Hurley | 437/249 |
| 5,754,717 | 5/1998 | Esch | 385/31 |
| 5,764,409 | 6/1998 | Colvin | 359/382 |

FOREIGN PATENT DOCUMENTS

| | | |
|---|---|---|
| 0 676 653 A1 | 10/1995 | European Pat. Off. . |
| 56074209 | 6/1981 | Japan . |
| 63267902 | 11/1988 | Japan . |
| WO 93/14432 | 7/1993 | WIPO . |

OTHER PUBLICATIONS

James Colvin; ESD Failure Analysis Methodology; Microelectronics Reliability; Nov. 1998; vol. 38; No. 11; pp. 1705–1714.

Primary Examiner—John D. Lee
Assistant Examiner—Sarah N Song
Attorney, Agent, or Firm—Smith & Danamraj, P.C.

[57] ABSTRACT

An emission microscopy system with a coherent illuminator system and method wherein an incident energy beam is directed at an end of image conduit rotating around its axis. The incident energy beam may be generated by a laser or similar radiation source. A substantially cylindrically uniform radiation spot is obtained from the other end of the image conduit, which may be guided by waveguide means to an emission microscope used in IC failure analysis.

15 Claims, 5 Drawing Sheets

EMISSION MICROSCOPY SYSTEM AND METHOD

PRIORITY UNDER 35 U.S.C. §119(e) & 37 C.F.R. §1.78(a)

This nonprovisional application claims priority based upon the following prior U.S. Provisional Patent Application entitled "Coherent Illuminator," Serial No. 60/087,553, filed Jun. 1, 1998, in the name of James Barry Colvin.

CROSS-REFERENCE TO RELATED APPLICATIONS

This nonprovisional application discloses subject matter that is related to the following patent application, concurrently filed herewith, entitled "Coherent Illumination System and Method" (Attorney Docket No. 1239-0001, U.S. application Ser. No. 09/181,261, filed Oct. 28, 1998.

BACKGROUND OF THE INVENTION

1. Technical Field of the Invention

The present invention relates to emission microscopy systems used in semiconductor integrated circuit (IC) failure analysis. More particularly, and not by way of any limitation, the present invention is directed to an emission microscopy system that includes a source for coherent and substantially uniform radiation or illumination.

2. Description of Related Art

Light (or photon) emission microscopy is a common failure analysis technique used for analyzing semiconductor integrated circuit (IC) devices. The considerations involved in using photon emission to successfully analyze defects and failure mechanisms in CMOS ICs are well known. IC failure analysis using an emission microscope is performed by collecting visible (390–770 nm), and sometimes near infrared (NIR) (770–1000 nm, with the typical IR band defined as 770–1500 nm), wavelength photons emitted from transistors, p/n junctions, and other photon-generating structures on or near the top (front), electrically-active, silicon surface. These photons are transmitted through the overlying, relatively transparent dielectric layers, passing between or scattered around the patterned, opaque metal interconnections. Detection of photons that emerge from around these overlying layers is referred to as frontside light emission analysis. Correspondingly, imaging light passing through the silicon substrate and emerging from the bottom (back) is referred to as backside light emission analysis.

Custom and commercial systems are routinely used for light emission analysis. The spectral characteristics for these systems are usually dependent upon the type of detector chosen. Most commercial systems use detectors based on image intensifiers or CCD arrays. Although current systems can provide detectors with extended NIR capability for backside analysis, most systems have very low response to photons with wavelengths beyond 1 $\mu$m.

There is an increasing interest in backside light emission analysis. This is driven primarily by the advancement of IC fabrication technologies with additional opaque conductor layers and packaging technologies that typically obscure the active side of the die. Backside analysis takes advantage of silicon's transmission of photons with energies less than its indirect silicon bandgap energy, corresponding to wavelengths greater than around 1.107 $\mu$m (for undoped silicon). It is commonly known that silicon becomes less transparent as dopants are added. Because of this phenomenon, the heavily doped substrates often used with newer technologies will attenuate NIR light emitted from the active circuits. These and other factors are stimulating research for solutions, including improved substrate thinning techniques, increased NIR imaging sensitivity, and spectral analysis.

It is well known that different types of photon emission processes can be distinguished by their spectra. Photon emission from defects or abnormal operation of silicon microelectronic devices generally falls into the following categories: forward or reverse biased p/n junctions, transistors in saturation, latchup, and gate oxide breakdown. While radiative recombination emission from silicon structures is generally centered around 1.1 $\mu$m, commonly used cameras have spectral response centered in the 400–900 nm range and can thus capture only a small portion of the emitted light.

Traditional methods of NIR imaging use an optical filter in conjunction with a broad-spectrum illuminator such as a quartz halogen bulb. The desired wavelengths pass through the filter and are used in the microscope illuminating path. The desired wavelength is selected by the filter when the unwanted light frequencies are rejected. One of the problems of the current technologies is that when a more intense illumination source is used to address at least in part the issue of the poor quantum efficiency of backside emission, the optical filters get degraded or destroyed quickly due to heating. The problem is further compounded by the fact that as the filter bandwidth is narrowed, the total energy is also reduced from the source output. On the other hand, employing longer integration times, by taking the emitted light inputs over a considerable period of time, negatively impacts the through-put. Due to these constraints, it can be appreciated that the current illumination technology cannot provide intense, narrow bandwidth illumination that is highly advantageous in backside emission analysis.

Laser sources can provide very intense, substantially monochromatic illumination. When these sources are used in backside emission analysis, however, interference phenomena cause what is commonly known laser "speckle" that blur the illuminated image. The speckle is seen at least in part due to the nonuniform distribution of radiation energy, giving rise to "hot spots" and "dark areas". While techniques such as diffusing the laser light using a frosted glass, dithering (i.e., scanning the laser beam), et cetera, are sometimes used, they have not been sufficiently effective in alleviating the speckle problem in backside emission imaging. Further, it may be appreciated that the recent popularity of flipchip technologies, rapid escalation in the number of metal interconnect layers and advanced packaging techniques (for example, ball grid arrays, land grid arrays, etc.)—all of which obscure the front side view of the active area—make the need to solve the speckle problem more acute.

SUMMARY OF THE INVENTION

The present invention overcomes these and other various deficiencies, shortcomings and drawbacks prevalent in current emission microscopy systems and attendent radiation/illumination technologies. The present invention advantageously provides a coherent illuminator system and method usable in a host of applications such as, for example, emission microscopy in IC failure analysis.

It should be understood that as used herein the term "illumination" is synonymous with the term "radiation" and pertains to any portion of the electromagnetic radiation spectrum. Accordingly, visible frequencies, microwave sources, X-ray sources and other radiation sources such as, e.g., particle accelerators with various spectra, are intended to be within the ambit of the present invention.

In one exemplary embodiment, the present invention is directed to an emission microscopy system, comprising: illuminator means for producing a substantially uniform illumination; and means for guiding the substantially uniform illumination to a microscope adapted for IC failure analysis. In one aspect, the illuminator apparatus means comprises: at least one radiation source (for example, a laser or similar coherent source) for producing incident radiation at a frequency; and an image conduit having a first terminus and a second terminus, which image conduit is rotatable around an axis associated therewith, wherein when the incident radiation is provided to the first terminus and the image conduit is rotated at an angular velocity, substantially uniform radiation, denoted herein as emergent radiation, is emanated from the second terminus.

In a yet another embodiment, the present invention relates to a method for generating a substantially cylindrically uniform radiation pattern, comprising the steps of: providing a radiation source for producing energy at a select frequency; providing an image conduit having a first terminus and a second terminus; applying the energy to the first terminus; and while the energy is applied at the first terminus, rotating the image conduit around its longitudinal axis at an angular velocity, whereby the substantially cylindrically uniform radiation pattern is emanated from the second terminus of the image conduit.

In another aspect, the present invention relates to an emission microscopy system, comprising: an illumination source for producing substantially uniform illumination, comprising: at least one laser for producing incident illumination at a frequency; an image conduit having a first terminus and a second terminus, the image conduit rotatable around an axis associated therewith; means for applying the incident illumination to the first terminus; and means for rotating the image conduit around the axis; and means for directing the substantially uniform illumination to a microscope, which illumination emanates from the second terminus when the incident illumination is applied at the first terminus and the image conduit is rotated.

BRIEF DESCRIPTION OF THE DRAWINGS

A more complete understanding of the method and apparatus of the present invention may be had by reference to the following Detailed Description when taken in conjunction with the accompanying Drawings wherein.

DETAILED DESCRIPTION OF THE DRAWINGS

Figure 1:
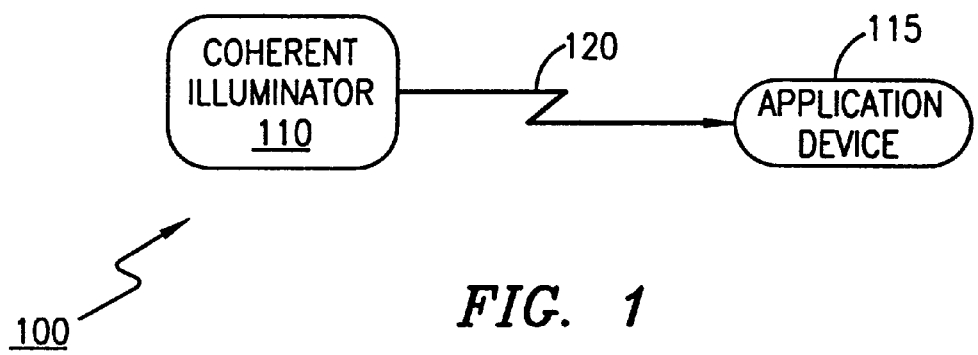
FIG. 1 depicts a system-level functional block diagram using a coherent illuminator source for an application, which source is provided in accordance with the teachings of the present invention.

Referring now to the Drawings wherein like or similar elements are designated with identical reference numerals throughout the several views, and wherein the various elements depicted are not necessarily drawn to scale, an more particularly to FIG. 1, shown therein is a system-level functional block diagram for an application system 100 using a coherent illuminator source 110 provided in accordance with the teachings of the present invention. The output or emergent radiation (or emergent illumination, if in visible spectra), which is substantially uniform and free of "hot spots", emanating from the illuminator source 110, is provided to an application element 115 via suitable conveying means 120 such as, for example, light guides, wave guides, fiber cables, fiber optics or optical fibers and hollow tubules with internal reflective surfaces and the like. The application element 115 is application-specific and can comprise an emission microscope used in semiconductor IC failure analysis. In further embodiments, the application element 115 can also comprise a medical instrument used in, for example, fiber optic phototherapy, photodynamic therapy, et cetera.

Figure 2:
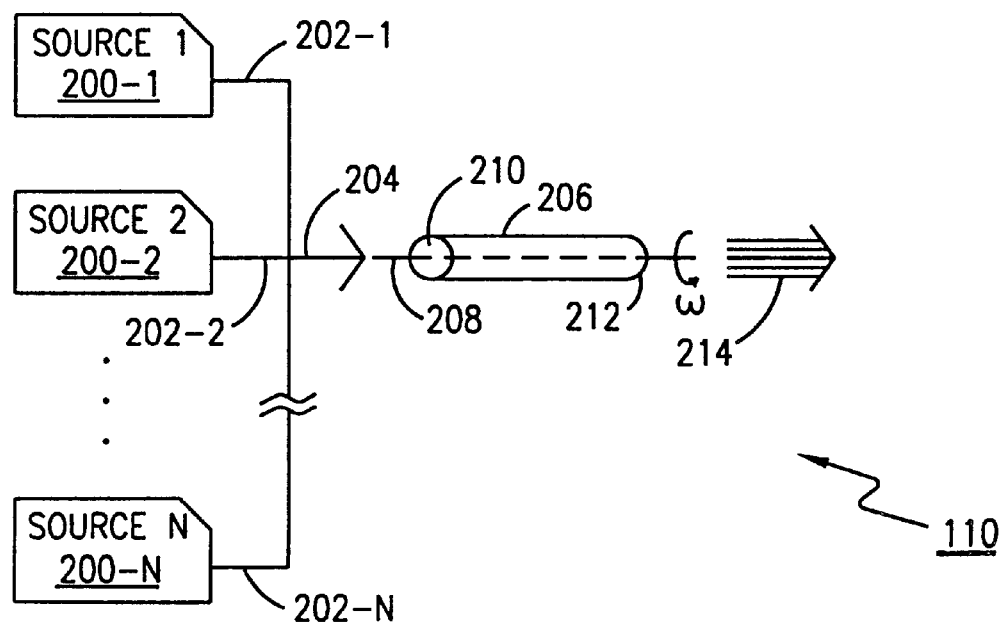
FIG. 2 illustrates a functional block diagram of an exemplary embodiment of a coherent illuminator source in accordance with the teachings of the present invention.

Referring now to FIG. 2, an exemplary embodiment of the coherent illuminator source 110 is shown in accordance with the teachings of the present invention. One or more radiation sources, labeled herein with reference numerals 200-1 through 200-N, are provided for generating radiation at suitable frequencies. Depending upon a particular application, one or more of these frequencies may be different and, accordingly, any number of frequency combinations may be provided. In one embodiment, the sources 200-1 through 200-N may comprise laser devices capable of producing illumination or radiation that is typically very intense, coherent, and almost perfectly parallel and monochromatic. In another embodiment, these sources may comprise maser devices (devices for microwave amplification through stimulated emission of radiation), producing energy radiation with substantially similar properties set forth above. In yet another embodiment, the radiation sources may include x-ray devices.

Radiation from the sources 200-1 through 200-N is provided via beam paths 202-1 through 202-N, respectively, to a first end or terminus 210 of an image conduit 206. Although separate paths 202-1 through 202-N are shown in this FIG., it should be understood by those skilled in the art that these radiation paths may overlap in any suitable combination. Further, although only one combined incident radiation beam path 204 is shown, any number of sub-combination paths may be provided to the terminus 210.

Continuing to refer to FIG. 2, the image conduit 206 can comprise a fiber rod, fiber bundle, or hollow tubules with internal reflective surfaces and the like. The cross-section of the image conduit 206 can take a variety of shapes, for example, circular, hexagonal, square, triangular, or polygonal shapes. The cross-sectional surface at the first terminus 210 may preferably be beveled so that the combined incident radiation or radiation path 204 is provided to the terminus 210 at a skew angle with respect to the longitudinal axis 208 of the image conduit 206. In a similar fashion, the other terminus 212 of the image conduit 206 may also be beveled at some angle, although it is not necessary for the purposes of the present invention. The length of the image conduit 206, furthermore, may vary to suit a particular application system.

In general operation, the image conduit 206 is rotated about or around its longitudinal axis 208 at an angular velocity ω in either clockwise or counter-clockwise direction, when the incident radiation beam 204 is applied at the first terminus 210. The emergent radiation beam 214 emanating from the second terminus 212 is a beam of homogenized radiation with substantial circumferential and/ or cross-sectional uniformity of intensity. Accordingly, the emergent radiation 214 is typically devoid of such artefacts as "dark areas", "hot spots" or "speckle" and the like found in current illumination technology, as dictated by the rotational speed of the image conduit 206.

Figure 3A:
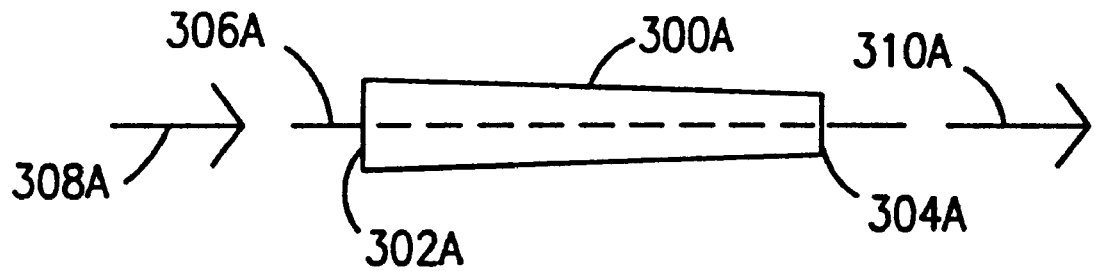
FIGS. 3A and 3B depict further exemplary embodiments of an image conduit provided in a coherent illuminator.
Figure 3B:
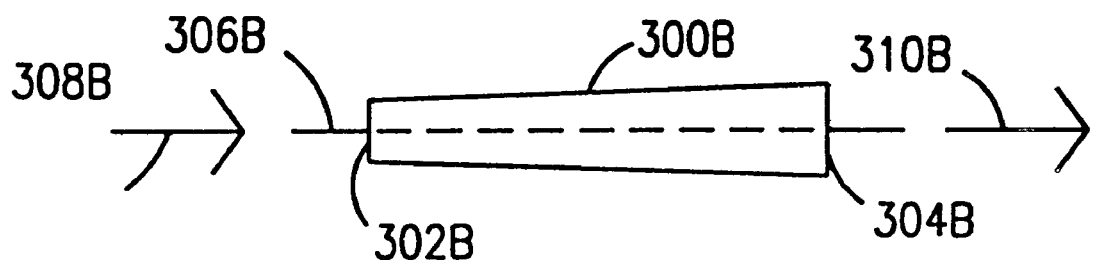

Referring now to FIGS. 3A and 3B, certain other embodiments of an image conduit, 300A and 300B, respectively, are shown. Both image conduits 300A and 300B are tapered. The cross-sectional area of the first terminus 302A of the conduit 300A is provided to be larger than the cross-sectional area of the other terminus 304A. In this embodiment, the incident radiation 308A is applied at the larger cross-sectional area (that is, lower numerical aperture) of the first terminus 302A. Once again, the incident radiation path may be at an angle with the longitudinal axis 306A of the image conduit 300A.

The first terminus 302B of the image conduit 300B is provided with a smaller cross-sectional area than that of the other terminus 304B. The incident beam 308B is applied at the smaller cross-sectional area (that is, higher numerical aperture) of the first terminus 302B. The emergent beam 310B is emanated from the second terminus 304B, substantially parallel to the longitudinal axis 306B of the image conduit 300B.

Whereas both image conduits 300A and 300B may be operable in certain exemplary application systems provided in accordance with teachings of the present invention, superior results are obtained when the incident radiation is applied at the terminus having higher numerical aperture, that is, by employing the conduit embodiment 300B. Very little speckle is produced in the emergent radiation 310B, even with very little or no angular velocity at which the conduit 300B is rotated. Accordingly, it should be appreciated that in some exemplary applications where rotation of image conduits is undesirable the tapered conduits disclosed herein may be advantageously provided in accordance herewith.

When the image conduits 300A and 300B are provided as rigid glass fiber rods, they may be referred to as fiber tapers. Those skilled in the art should appreciate upon reference hereto that both tapered and non-tapered image conduits may also be provided as cores with high index of refraction surrounded by suitable cladding materials of low index.

Figure 4:
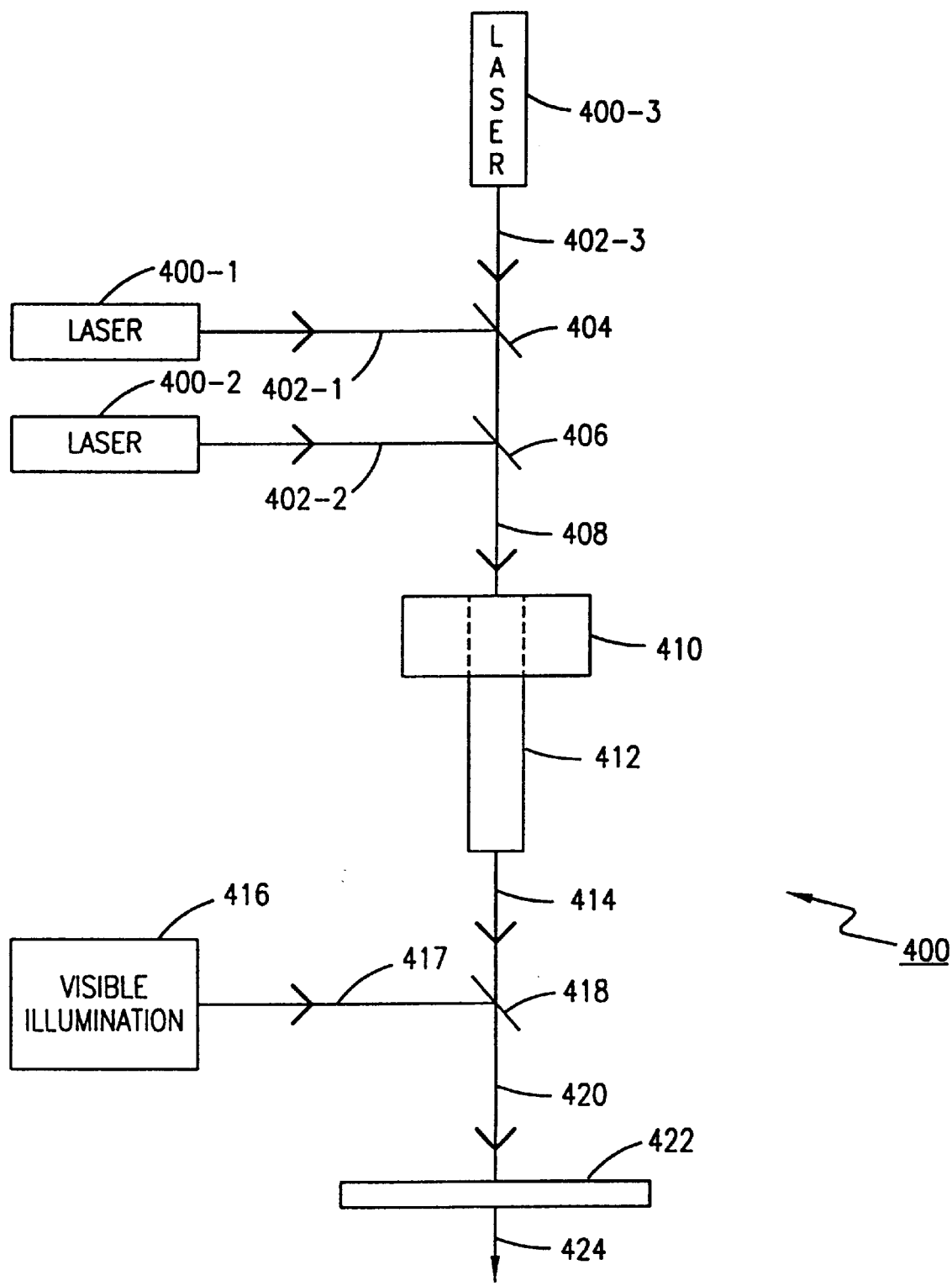
FIG. 4 is a functional block diagram of a presently preferred exemplary embodiment of a coherent illuminator source in accordance with the teachings of the present invention.

Referring to FIG. 4, a functional block diagram of a presently preferred exemplary embodiment of a coherent illuminator source 400 is shown in accordance with the teachings of the present invention. Two laser sources, preferably at 1064 nm and labeled with reference numerals 400-1 and 400-2, are provided for generating a portion of the incident radiation 408. The radiation beam 402-1 from the laser source 400-1 is directed at a first gold mirror 404. Similarly, the radiation beam 402-2 from the laser source 400-2 is directed at a second gold mirror 406. In this presently preferred embodiment, the gold mirrors 404 and 406 are mounted at a 45° angle with respect to the paths of the radiation beams 402-1 and 402-2. A third laser source, preferably at 670 nm and labeled with reference numeral 400-3, is provided for generating another portion of the incident beam 408. The beam 402-3 emanating from the laser source 400-3 does not have to pass through the gold mirrors 404 and 406. Instead, the beam 402-3 may be directed over the mirrors 404 and 406. Therefore, it should be understood upon reference hereto that the incident beam 408 may comprise one or more sub-combinations of beams whose paths may or may not necessarily overlap one another or be "fused" together.

A dynamic scanner 410 is provided for rotating a fiber rod image conduit 412 that is affixed thereto. The scanner 410 preferably comprises a Toshiba LSM-206-8D or an equivalent laser scanner motor. This presently preferred motor embodiment is a precision bearing motor operable at 24 volts and at about 7700 rpm. The motor's angular velocity (spin rate) or speed does not have to be at this rate; advantageous results are obtained even with low spin rates, for example, a few hundred rpm. One of ordinary skill in the art may appreciate that any suitable motor can be used for the spinning function, with obvious modifications if necessary.

The fiber rod image conduit 412 is preferably about 3 inches long and 0.250 inches in diameter from Edmund Scientific, with part nos. D53848 or D53842 (high resolution). The fiber rod 412 may be appropriately machined or altered to suit the securing mechanisms (not shown) of the scanner motor 410. In the presently preferred exemplary embodiment, the motor shaft is replaced with the suitably machined fiber rod 412.

While only three laser sources are shown in this FIG., multiple lasers can be aimed at the terminus end (not shown) of the fiber rod 412 exposed to the incident beam 408. As is known in the art, the angular size of the energy exiting the fiber rod conduit 412 can be a function of the entry angle of the incident beam 408. If the incident beam is perfectly parallel to the axis of the fiber rod 412, internal reflections may not be possible provided the rod is dimensionally ideal. However, in practice, manufacturing variations, and the length of the fiber rod 412 relative to the small diameter of the individual fibers typically render such concerns somewhat moot.

Preferably, a small skew angle between the incident radiation beam 408 and the vector perpendicular (normal) to the face of the terminus may be, accordingly, provided by beveling the terminus face. On the other hand, if the terminus face is not beveled, a skew angle may be provided in the incident beam path by suitable means such as wave or light deflectors and the like.

Continuing to refer to FIG. 4, the incident radiation 408 passes through the spinning fiber rod 412 (in either clockwise or counter-clockwise direction) and exits from the other terminus thereof as emergent radiation 414. In some aspects, the emergent radiation 414 may directly be provided through suitable conveying means, for example, light guides, fiber cables, optical fibers (as used herein, the term "optical fiber" is intended to encompass optically transmissive waveguides of various shapes and sizes), hollow tubes or tubules, and the like, to an application element (not shown in this FIG.) specific for the particular use. In the embodiment shown in FIG. 4, the emergent radiation 414 passes through a pass-through mirror 418 provided at a 45° angle thereto. A visible illumination source 416, preferably a quartz halogen light source, is provided for generating a visible light beam 417 which is directed at the mirror 418. The visible light 417 is reflected off the mirror 418 and is combined with the emergent radiation 414 to give rise to an output beam 420. The pass-through mirror 418 is referred to as a "cold" mirror because it transmits the laser energy while the visible light is reflected off its surface. The output beam 420 may be directed through a filter wheel 422 that is controlled by suitable control means (not shown) (for example, a push rod or other electro-mechanical devices) to select different colors. The exit beam 424 from the filter 422 is provided to conveying means (not shown) such as those discussed hereinabove for transmitting the exit beam 424 to a point of application, for example, as an illumination reference for an emission microscope used in IC failure analysis. A black and white camera provided with the microscope can take color images of the illuminated reference image of the IC because of the color selection by the filter wheel mechanism 422.

Figure 5:
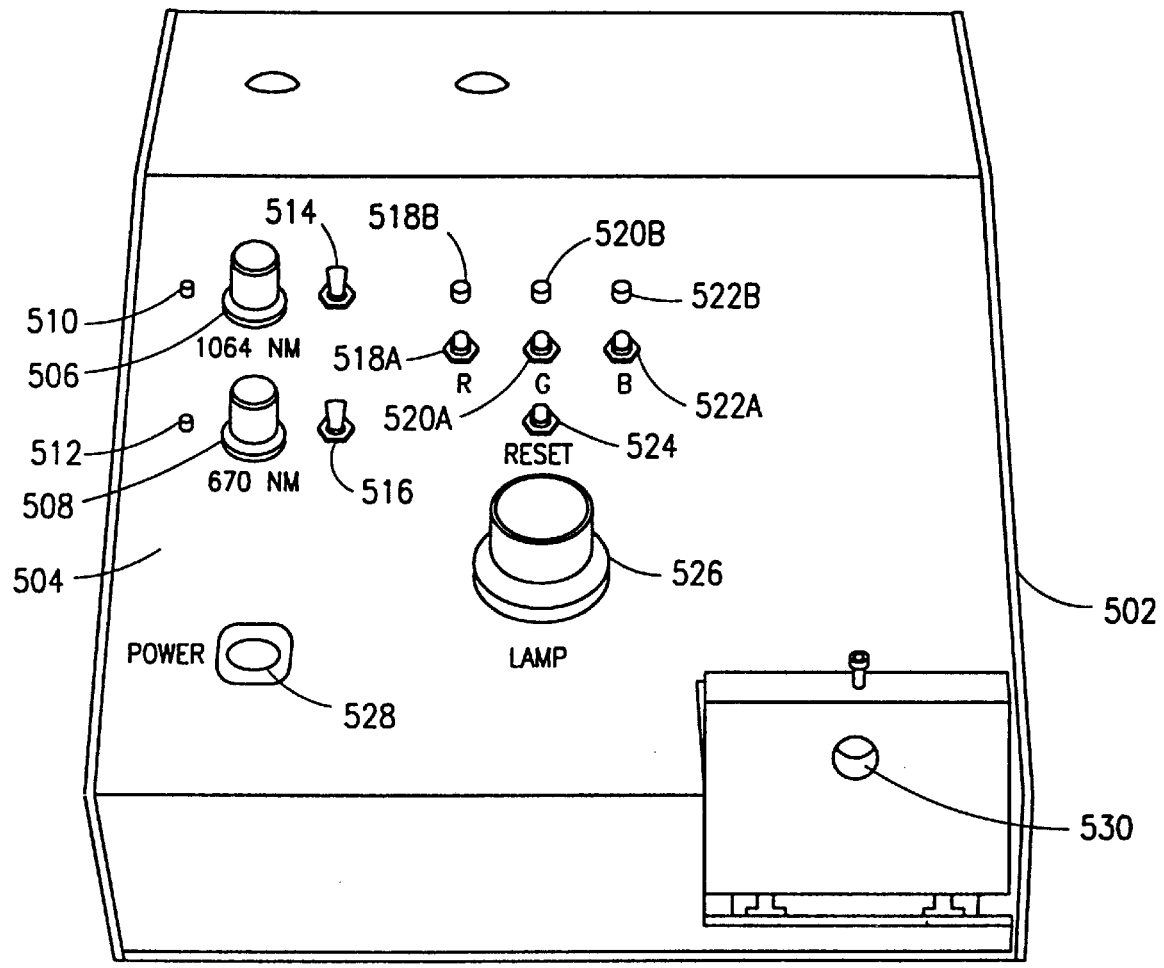
FIG. 5 is an external view of a coherent illuminator system embodying the teachings of the present invention.

Referring now to FIG. 5, shown therein is an external view of a coherent illuminator apparatus 500 embodying the teachings of the present invention described in reference to FIG. 4. On the front panel 504 of the chassis 502, a plurality of control knobs and switches are disposed. A power switch 528 is provided for turning on or off the apparatus 500. A control knob 506 is provided for controlling the 1064 nm laser sources. An associated indicator 510 is depicted. A control knob 508 is provided for controlling the 670 nm laser source along with its associated indicator 512. Separate on/off switches, labeled with reference numerals 514 and 516, are provided in connection with the laser sources.

A visible lamp control knob 526 is provided for controlling the quartz halogen projector lamp. Primary color filters associated with the filter wheel (shown in FIG. 4) are controlled by switches 518A (for RED), 520A (for GREEN) and 522A (for BLUE). Associated indicators, 518B, 520B and 522B, respectively, are also shown. An exit orifice 530 is provided with the illuminator apparatus 500 for allowing the passage of the emergent radiation or the exit beam, as necessary.

Figure 6:
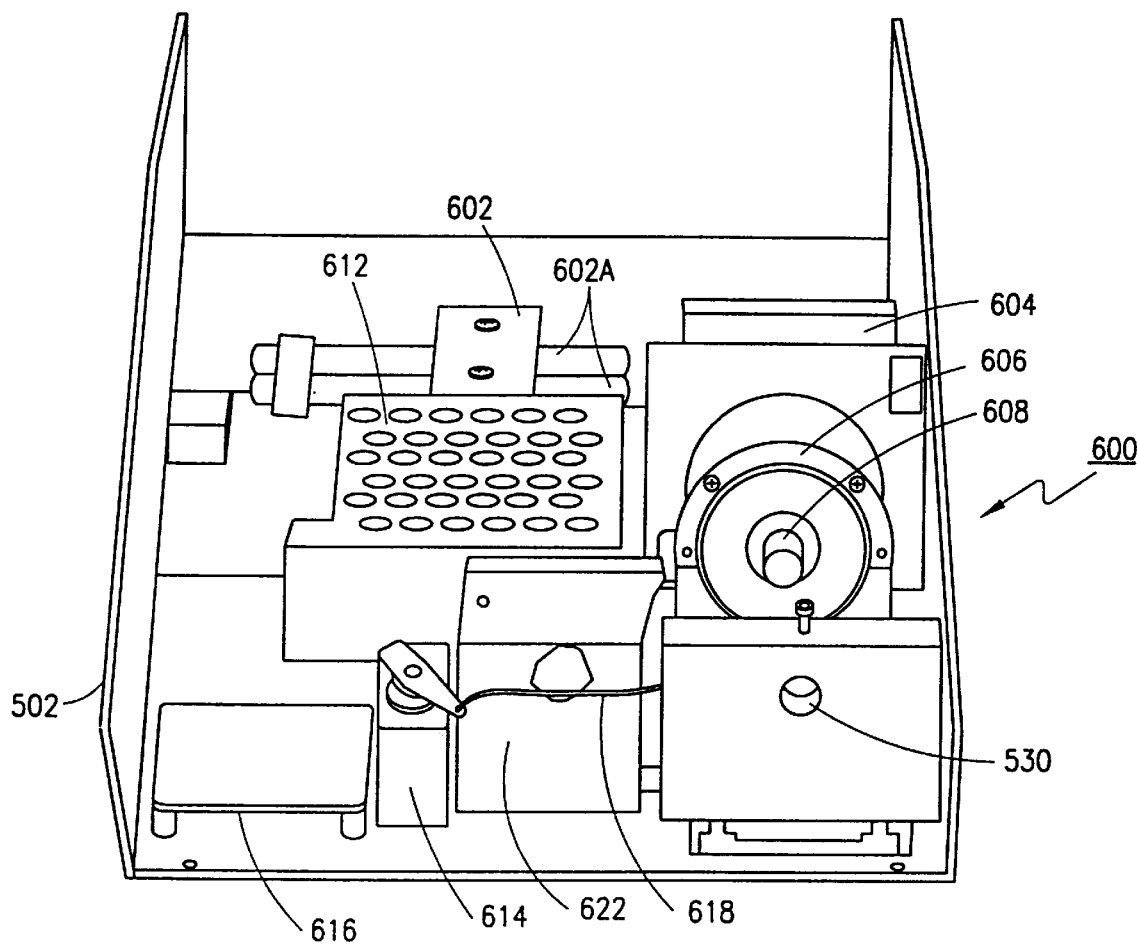
FIG. 6 is an internal view of the coherent illuminator system depicted in FIG. 5.

FIG. 6 depicts an internal view 600 of the illuminator apparatus 500 described above with the front panel 504 removed. A laser bracket 602 secures two 1064 nm diode pumped continuous wave lasers 602A. A mounting bracket 604 is provided for securing a 670 nm laser diode (not shown). Although not shown in this FIG., a pair of gold mirrors are provided near or below the bracket 604 for directing the laser energy from the lasers 602A. A switching power supply 612 is provided for supplying power to the lasers. A dynamic scanner motor 606 with a speed control electronics board behind it is provided for spinning an image conduit fiber rod 608. A control electronics board 616 which includes conventional circuitry (for example, oscillators, timers, flip-flops and latches) is also provided. A servo motor 614 is provided for controlling the position of the filter wheel (not shown) via a push rod mechanism 618. A shield 622 is provided around the quartz halogen projector lamp (not shown) for reducing the heat and unwanted radiation emanated therefrom. The exit orifice 530 is provided for passing the emergent radiation (or output beam) emanated from the fiber rod 608. Although not shown in this FIG., it should be realized that a suitable cold mirror arrangement is provided in the emergent beam path.

Based on the foregoing Detailed Description, it should be appreciated that the present invention provides an efficient system for producing substantially cylindrically and/or circumferentially uniform radiation usable in a multitude of applications. The invention allows a laser, maser or similar coherent source to be used as a high brightness illuminator for industrial, scientific, nuclear, or medical applications which require a concentrated but uniform illumination scheme using monochromatic radiation sources.

Although certain preferred embodiments of the method and apparatus of the present invention have been illustrated in the accompanying Drawings and described in the foregoing Detailed Description, it will be understood that the invention is not limited to the embodiments disclosed, but is capable of numerous rearrangements, modifications and substitutions without departing from the spirit of the invention as set forth and defined by the claims set forth hereinbelow. For example, multiple wavelengths can be independently or simultaneously injected through the spinning image conduit. It should be realized that a square rod or fiber bundle with polished ends spinning on its axis serves the same function as the image conduit described hereinabove in accordance with the teachings of the present invention. Additionally, hollow tubules that achieve similar total internal reflection as the light guides with high refractive index core and low index cladding may also be used. Adding a bevel angle at one or both ends of the image conduit may also help alleviate second order effects such as reflection of the polished ends. Rough polishing and frosting one or both ends may be used for accomplishing the same purpose, although some of the radiant energy may be lost because of scattering or diffusion.

Furthermore, as can be realized upon reference hereto, the image conduit of the illuminator apparatus of the present invention may be provided with a variety of shapes and forms having different cross-sectional areas. Tapered fiber rods may also be used for this purpose. Although the teachings of the present invention have been exemplified for the most part with laser sources, it should be clear to one of ordinary skill in the art that any portion of the electromagnetic spectrum may be used as a source within the scope hereof. Moreover, any conventional optical arrangements such as, for example, mirrors, lenses, beam splitters, prisms, et cetera, may be used to direct either the incident or emergent or both energy beams. Accordingly, all such and other rearrangements, modifications and substitutions are deemed to comprise the teachings of the present invention whose scope is defined by the following claims.

What is claimed is:

1. A emission microscopy system, comprising:
    an illuminator source having a rotatable image conduit for producing a substantially uniform illumination pattern; and
    means for guiding said substantially uniform illumination pattern to a microscope adapted for emission analysis.

2. The emission microscopy system as set forth in claim 1, wherein said illuminator source comprises:
    at least one radiation source for producing incident radiation at a frequency; and
    said image conduit having a first terminus and a second terminus, said image conduit being rotatable around a longitudinal axis associated therewith, wherein when said incident radiation is provided to said first terminus and said image conduit is rotated with an angular velocity at least greater than or equal to zero, said substantially uniform illumination pattern, denoted herein as emergent radiation, is emanated from said second terminus.

3. The emission microscopy system as set forth in claim 2, wherein said means for guiding comprises a fiber optic cable.

4. The emission microscopy system as set forth in claim 1, wherein said illuminator source comprises:
    at least one radiation source for producing incident radiation at a frequency; and
    said image conduit having a select shape, a first terminus and a second terminus, said image conduit being selectively rotatable around a longitudinal axis associated therewith, wherein when said incident radiation is provided to said first terminus and said image conduit is rotated with an angular velocity dependent upon said shape, said substantially uniform illumination pattern, denoted herein as emergent radiation, is emanated from said second terminus.

5. The emission microscopy system as set forth in claim 4, wherein said image conduit comprises a fiber taper and said first terminus has a higher numerical aperture than that of said second terminus.

6. The emission microscopy system as set forth in claim 5, wherein said angular velocity is substantially equal to zero.

7. The emission microscopy system as set forth in claim 4, wherein said image conduit comprises a fiber taper said second terminus has a higher numerical aperture than that of said first terminus.

8. An emission microscopy system, comprising:
   an illumination source for producing a substantially uniform illumination pattern, comprising:
      at least one laser for producing incident illumination at a frequency;
      an image conduit having a first terminus and a second terminus, said image conduit rotatable around an axis associated therewith;
      means for providing said incident illumination to said first terminus; and
      means for rotating said image conduit around said axis; and
   means for directing said substantially uniform illumination pattern to a microscope, which illumination pattern emanates from said second terminus when said incident illumination is applied at said first terminus while said image conduit is rotated.

9. The emission microscopy system as set forth in claim 8, wherein said image conduit comprises a fiber rod.

10. The emission microscopy system as set forth in claim 8, further comprising a visible light source.

11. The emission microscopy system as set forth in claim 10, further comprising a color filter.

12. In an emission microscopy system, an illumination method for providing illumination, comprising the steps of:
   generating a substantially uniform laser illumination pattern by rotating an image conduit around its longitudinal axis with an angular velocity depending upon said image conduit's shape, wherein an incident laser beam is provided to a first terminus of said image conduit; and
   transmitting said substantially uniform laser illumination pattern to an emission microscope via an optical guide.

13. The illumination method for use in an emission microscopy system as set forth in claim 12, wherein said image conduit comprises a substantially cylindrical fiber rod.

14. The illumination method for use in an emission microscopy system as set forth in claim 12, wherein said image conduit comprises a fiber taper.

15. The illumination method for use in an emission microscopy system as set forth in claim 12, wherein said angular velocity is substantially zero.

* * * * *